United States Patent [19]
Abidin et al.

[11] Patent Number: 5,361,902
[45] Date of Patent: Nov. 8, 1994

[54] SURGICAL BLADE DISPENSER AND DISPOSAL SYSTEM FOR USE DURING AN OPERATING PROCEDURE AND METHOD THEREOF

[75] Inventors: Michael R. Abidin; Steven P. Lehmbeck, both of Baltimore, Md.

[73] Assignee: Leonard Bloom, Towson, Md.; a part interest

[21] Appl. No.: 894,595

[22] Filed: Jun. 5, 1992

[51] Int. Cl.⁵ ............................................. B65D 83/10
[52] U.S. Cl. .................................. 206/370; 206/363; 206/354; 206/359
[58] Field of Search ............... 206/354, 359, 360, 363, 206/355, 370, 352; 29/239, 278

[56] References Cited

U.S. PATENT DOCUMENTS

| | | | |
|---|---|---|---|
| 3,447,181 | 6/1969 | Coker et al. | 206/363 |
| 3,543,918 | 12/1970 | Waterman | 206/359 |
| 4,106,620 | 8/1978 | Brimmer et al. | 206/363 |
| 4,120,397 | 10/1978 | Neumann | 206/370 |
| 4,180,162 | 12/1979 | Magney | 206/363 |
| 4,270,416 | 6/1981 | Thompson | 81/3 R |
| 4,344,532 | 8/1982 | Eldridge, Jr. et al. | 206/370 |
| 4,395,807 | 8/1983 | Eldridge, Jr. et al. | 29/239 |
| 4,523,679 | 6/1985 | Paikoff et al. | 206/363 |
| 4,730,376 | 3/1988 | Yamada | 29/239 |
| 4,746,016 | 5/1988 | Pollak et al. | 206/356 |
| 4,903,390 | 2/1990 | Vidal et al. | 29/239 |
| 5,088,173 | 2/1992 | Kromer et al. | 29/239 |

*Primary Examiner*—David T. Fidei
*Attorney, Agent, or Firm*—Leonard Bloom

[57] ABSTRACT

A sterile blade dispenser facilitates removal of dulled used blades, as well as the mounting of sharp unused blades, on a scalpel during a surgical procedure being conducted in an operating room or similar environment. Preferably, the scalpel has a sliding retractable guard, and the combination of the guarded scalpel and the blade dispenser precludes inadvertent cuts or nicks during the surgical procedure.

12 Claims, 12 Drawing Sheets

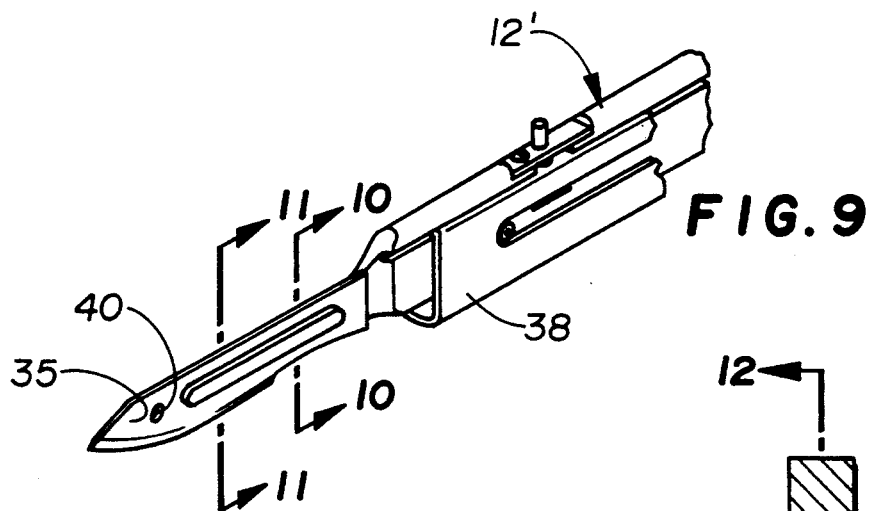
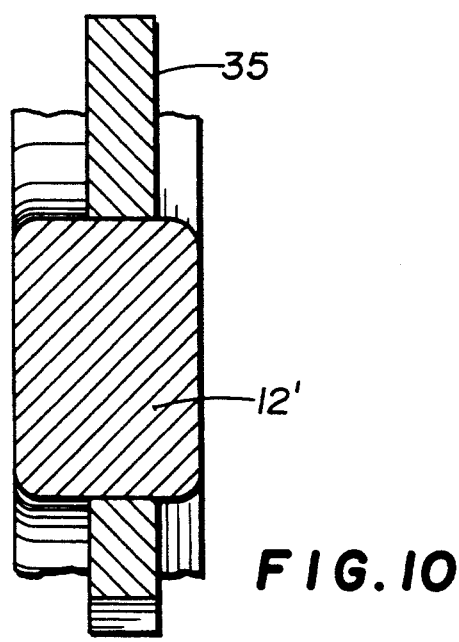
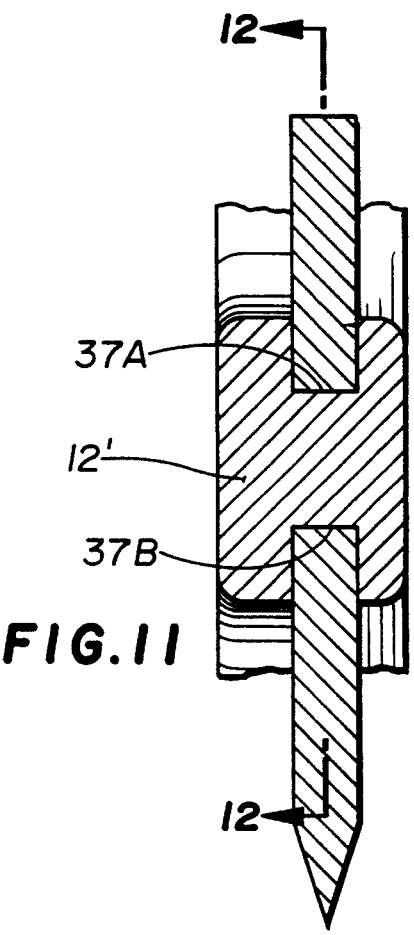
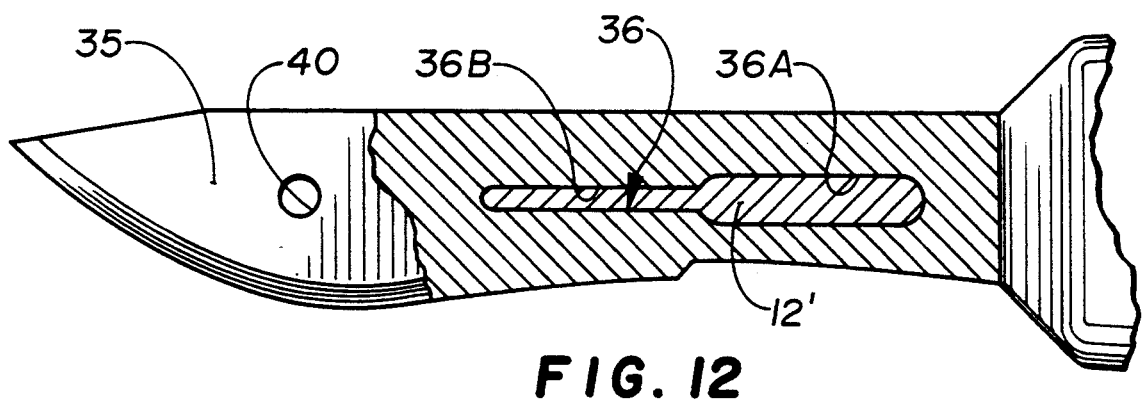

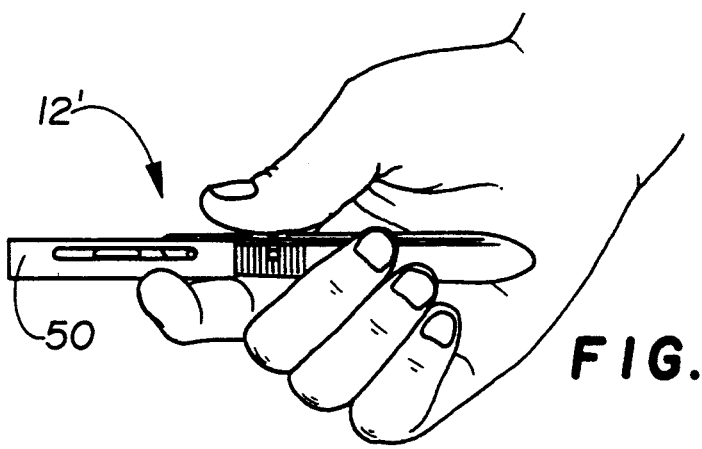
FIG. 15A
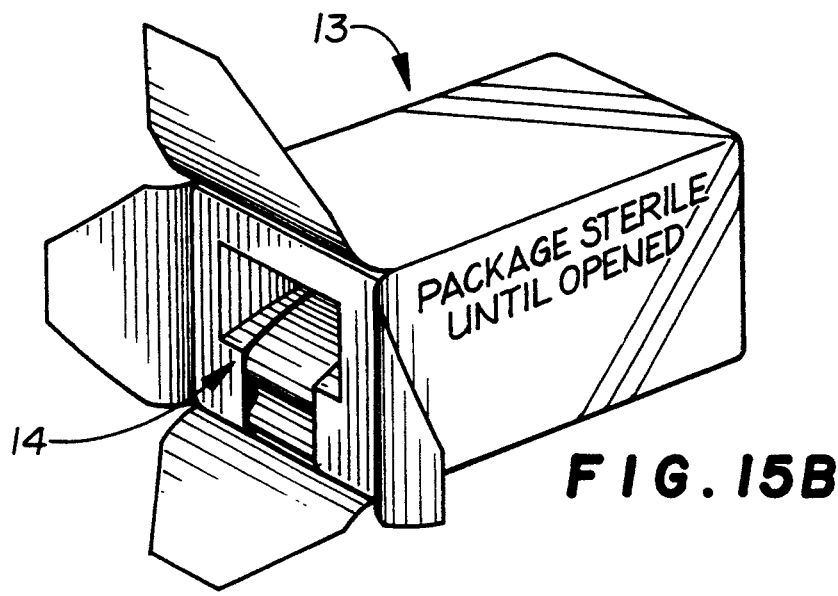
FIG. 15B
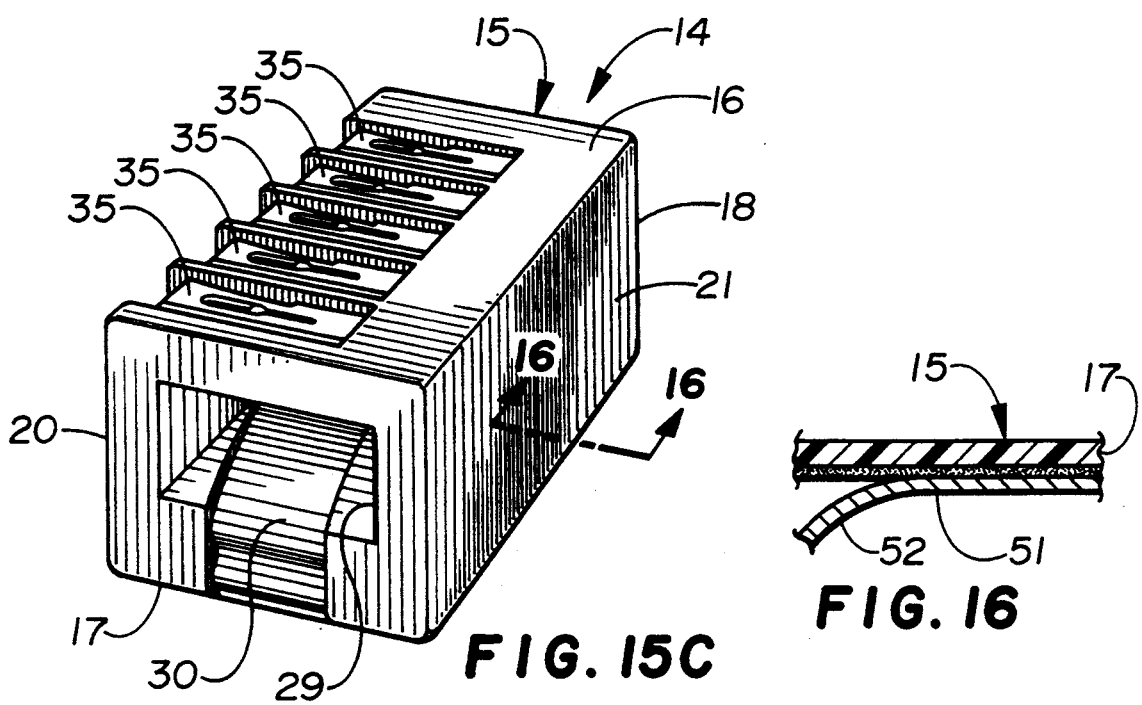
FIG. 15C
FIG. 16

ASSISTANT

SURGEON

SURGICAL BLADE DISPENSER AND DISPOSAL SYSTEM FOR USE DURING AN OPERATING PROCEDURE AND METHOD THEREOF

FIELD OF THE INVENTION

The present invention relates to a surgical blade dispenser and disposal system for use during an operating procedure, and more particularly, to a surgical blade dispenser and disposal system for use in conjunction with a guarded scalpel.

BACKGROUND OF THE INVENTION

Surgical blades on a scalpel are replaced several times during an operating procedure. On the average, about five new blades are used on each scalpel, depending upon the surgeon's techniques and preferences, the type of operation being performed, and the severity thereof. During the procedure, the blade can become dulled quite rapidly, especially if tissue or bone is being cut, and surgeons prefer to have a very sharp blade on the scalpel at all times.

Each blade is contained in a sterile package of aluminum foil or the like, and the package is peeled apart to uncover the rear portion of the blade. Typically, the rear portion of the blade has a longitudinal slotted opening formed therein to receive a laterally-projecting bar on the forward portion of the scalpel; and the bar on the scalpel is snapped into the slotted recess on the blade, thereby removably mounting the blade on the scalpel.

This is a manual operation. The used blade is removed from the scalpel, and a new blade is subsequently mounted on the scalpel, basically using finger dexterity, and sometimes using an instrument called a hemostat. Despite the care that is exercised, the nurse or other assistant in the operating room is occasionally cut or nicked while changing blades on a scalpel, especially while the nurse or assistant is concentrating on the patient or the instruments at critical times during the operating procedure.

The used blades often carry blood, tissue or bodily fluids, and thus there is a substantial problem that the nurse or other assistant in the operating room will inadvertently acquire an infectious disease, such as the Hepatitis B virus or the HIV ("AIDS") virus. The situation is becoming quite serious, if not alarming, and some health care providers have quit their operating room practice entirely rather than continually risking exposure to the AIDS virus.

SUMMARY OF THE INVENTION

Accordingly, it is an object of the present invention to provide a blade dispenser and disposal system that speeds up the process of changing blades during a surgical procedure in an operating room or the like, thereby assuring that the surgeon will at all times have a "fresh" sharp blade.

It is another object of the present invention to provide a surgical blade dispenser that is convenient and easy to use, reliable, and economical to manufacture.

In accordance with the teachings of the present invention, there is herein illustrated and described, a preferred embodiment of a blade dispenser and disposal system for use during a surgical procedure in an operating room or the like, wherein the blades on a scalpel are normally replaced during the procedure to maintain good surgical cutting techniques. The dispenser includes a housing, and a first means is provided within the housing to enable an existing blade to be removed from the scalpel upon insertion and withdrawal of the scalpel from the housing, the existing discarded blade being confined within the housing. At least one new blade is provided in the housing, and a second means is provided within the housing to enable the new blade to be mounted on the scalpel upon subsequent re-insertion of the scalpel into the housing and withdrawal of the scalpel therefrom. As a result, inadvertent cuts or the like are precluded as the blades are replaced on the scalpel during the surgical procedure.

In accordance with a preferred embodiment of the present invention, a sterile package is provided for the housing, the sterile package being removed prior to the surgical procedure.

Preferably, a plurality of new blades is contained within the housing; and the housing with the discarded blades confined therein, as well as any unused blades, is disposed of following the surgical procedure.

In accordance with the further teachings of the present invention, and fully compatible therewith, a guard is slidably mounted on the scalpel, the guard being alternatively retracted and advanced to uncover and cover the blade, respectively, all in a one-handed operation. As a result, inadvertent cuts or the like are precluded in passing the scalpel from the assistant to the surgeon, and vice-versa, during the surgical procedure.

Accordingly, the blade is exposed only when the scalpel is being used by the surgeon during the surgical procedure.

Viewed in another aspect, the present invention provides, in a surgical procedure in an operating room or the like, a method of changing blades on a scalpel during the surgical procedure and transferring the scalpel from an assistant to a surgeon during the procedure to avoid inadvertent cuts or the like. The inventive method including the steps of providing a sterile blade package and further providing a guarded scalpel. The sterile blade package is opened in the operating room, and the guard is moved on the scalpel to an unguarded "off" position. The unguarded scalpel is inserted into the package to strip an "old" or used blade from the scalpel. The stripped scalpel is removed from the package and re-inserted into the package to pick up a "new" or unused blade. The scalpel with the new blade is removed from the package, and the guard on the scalpel is moved to a guarded "on" position.

Viewed in yet another aspect, the present invention provides (for use with a surgical scalpel having a replaceable blade) the combination of a manually-operable guard means on the scalpel—such that the blade on the scalpel may be covered when the scalpel is transferred from the assistant to the surgeon (and vice versa) during a surgical procedure in an operating room in a hospital or similar environment—and a dual-purpose blade dispenser and collector for the disposal of old or used blades. The scalpel may be inserted into the dispenser to strip a used blade from the scalpel and to subsequently pick up a new unused blade, such that the blade is exposed only when the scalpel is being used by the surgeon during the procedure.

These and other objects of the present invention will become apparent from a reading of the following specification taken in conjunction with the enclosed drawings.

BRIEF DESCRIPTION OF THE DRAWINGS

FIG. 1 is a perspective of the lead surgeon, assistants and nurses performing a surgical procedure in an operating room in a hospital, clinic or the like.

FIG. 9 is a perspective view of a guarded scalpel with which the teachings of the present invention may find more particular utility, the guard being slidably retracted rearwardly of the scalpel to uncover the blade which is mounted on a forwardly-projecting portion of the scalpel.

FIG. 10 is a cross-sectional view, taken across the lines 10—10 of FIG. 9 and drawn to an enlarged scale, and showing the removable mounting of the blade on the forward portion of the scalpel.

FIG. 11 is a further cross-sectional view, taken across the lines 11—11 of FIG. 9 and drawn to an enlarged scale, and further showing the removable mounting of the blade on the scalpel.

FIG. 12 is a still further cross-sectional view, taken across the lines 12—12 of FIG. 11.

FIGS. 15A–15J are still further schematic sequence views, showing the overall procedure or method involving the preferred guarded scalpel, and basically showing how the guard on the scalpel is moved rearwardly to its unguarded "off" position to uncover the old or used blade, how the scalpel is inserted within the housing and withdrawn therefrom with the used blade removed, how the scalpel is subsequently re-inserted into the housing to pick up an unused blade, and how the guard on the scalpel is moved forwardly to its guarded "on" position, such that the guarded scalpel with its new blade may then be transferred from the nurse to the surgeon during the surgical procedure to avoid inadvertent (and hazardous) cuts and nicks, thereby avoiding the inadvertent acquisition of infectious diseases.

FIG. 16 is a section view, taken across the lines 16—16 of FIG. 15C, and showing an adhesive layer on the bottom of the blade dispenser to enable the blade dispenser to be removably mounted on a tray in the operating room.

GENERAL DESCRIPTION OF THE PREFERRED EMBODIMENTS

Figure 1:
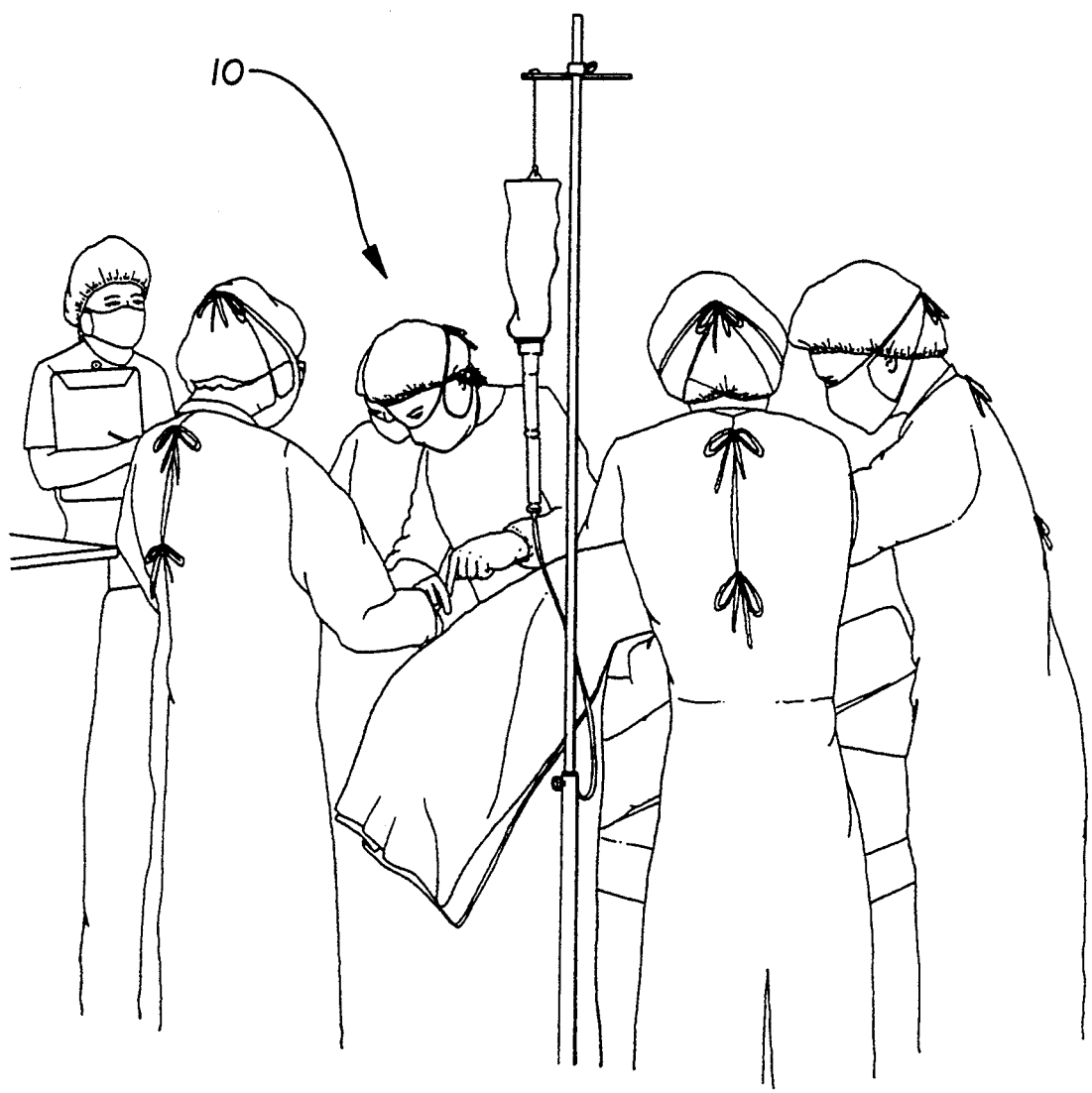
Figure 2:
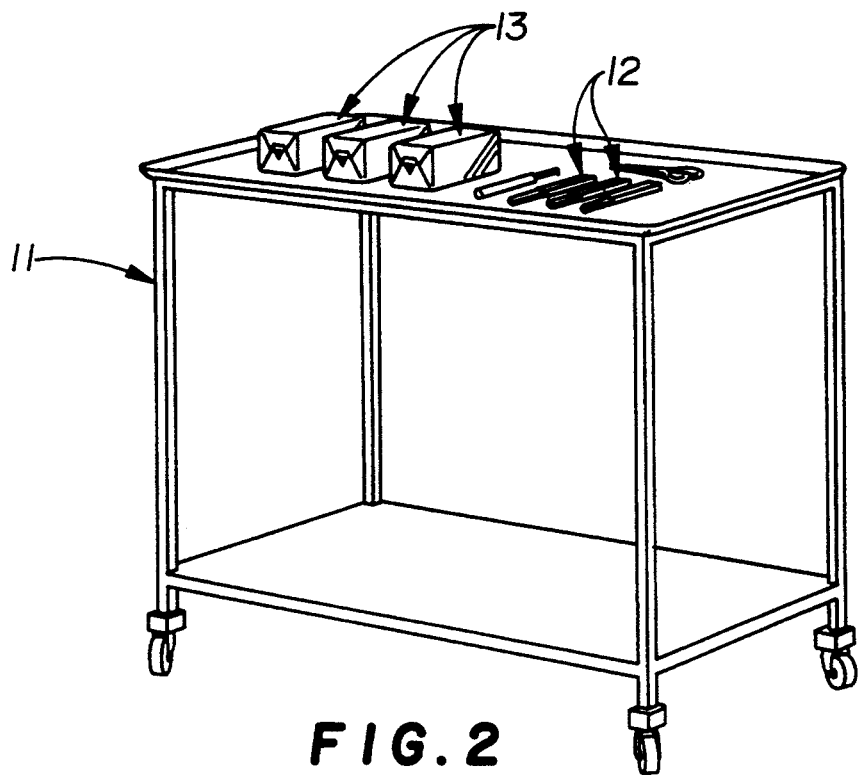
FIG. 2 is a perspective view of a typical wheeled cart used in the operating room to hold the various surgical devices and instruments, including one or more scalpels and one or more sterile blade packages of the present invention.
Figure 3:
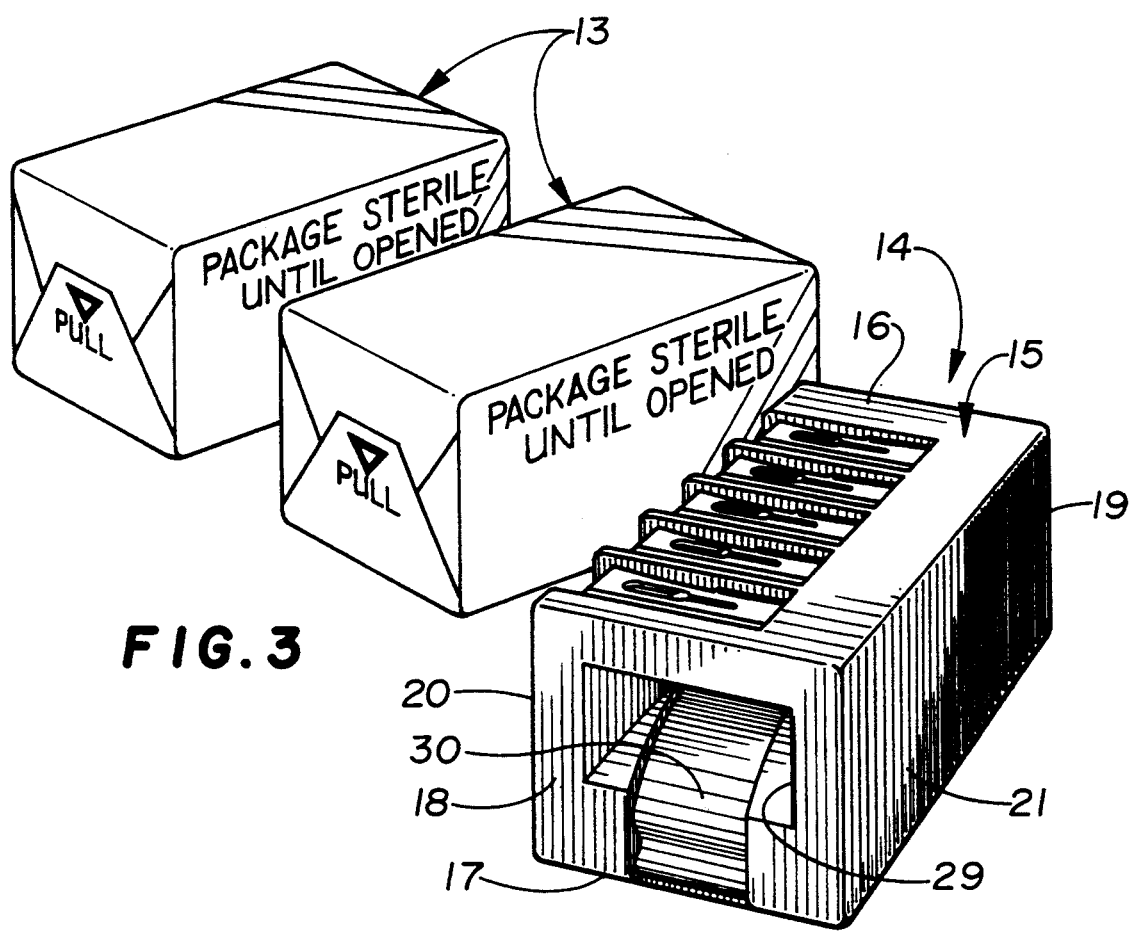
FIG. 3 is a perspective view of the sterile blade packages of FIG. 2, drawn to an enlarged scale, and further showing the sterile packaging removed from one of the packages to uncover the blade dispenser and collector of the present invention.
Figure 4:
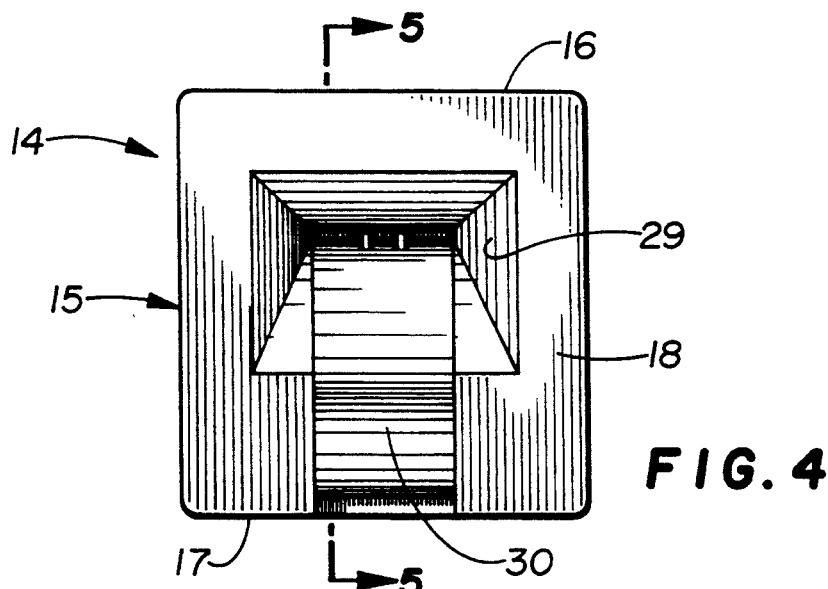
FIG. 4 is a front view of housing of the blade dispenser of FIG. 3, drawn to a somewhat enlarged scale.

With reference to FIGS. 1-3, the present invention is intended for use in an operating room 10 in a hospital, clinic or similar area. Within the operating room 10, there is usually a wheeled cart or tray 11 upon which the various surgical instruments or devices are placed. These devices include a number of scalpels 12 as well as the sterile blade packages 13 of the present invention. The packaging is removed from one of the sterile blade packages, as shows more clearly in FIG. 3, to uncover a blade cartridge or dispenser 14 of the present invention.

With reference again to FIG. 3, and with further reference to FIGS. 4–8, the blade dispenser 14 is preferably molded and fabricated from a suitable plastic material and is preferably oblong or rectangular in shape. However, it will be appreciated that the blade dispenser 14 may have any convenient size and shape and may be fabricated from a variety of suitable materials, if desired. With this in mind, the blade dispenser 14 includes a housing 15 having a top wall 16, a bottom wall 17, a front wall 18, a rear wall 19, a right side wall 20 and a left side wall 21.

Figure 5:
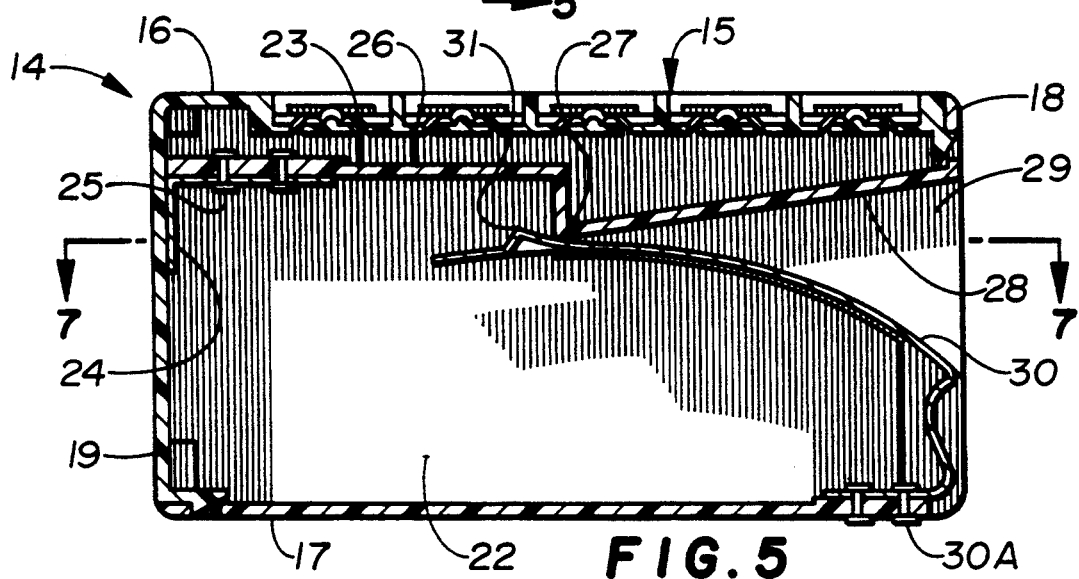
FIG. 5 is a cross-sectional view, taken along the lines 5—5 of FIG. 4, and showing an internal wall intended to cooperate with a leaf spring in the housing to remove an "old" or used blade from the scalpel.

As best shown in FIG. 5, the housing 15 has a chamber 22 for receiving the "old" or used blades. The housing 15 further has an internal wall 23 disposed below the top wall 16 and running from the rear wall 19 of the housing 15 to the front wall 18 thereof. Preferably, this internal wall 23 is molded from a suitable plastic material and is cantilever mounted on the rear wall 19 by means of an L-shaped bracket 24 suitably secured to the rear wall 19 and, in turn, to the internal wall 23 by rivets 25. The internal wall 23 includes a straight portion 26, a downwardly-projecting intermediate portion providing a shoulder 27, and an upwardly-sloping portion 28 terminating at the front wall 18 of the housing 15. The housing 15 has an opening 29 in its front wall 18 through which the scalpel may be inserted (as hereinafter described) to remove or strip the "old" or used blade from the scalpel.

Figure 7:
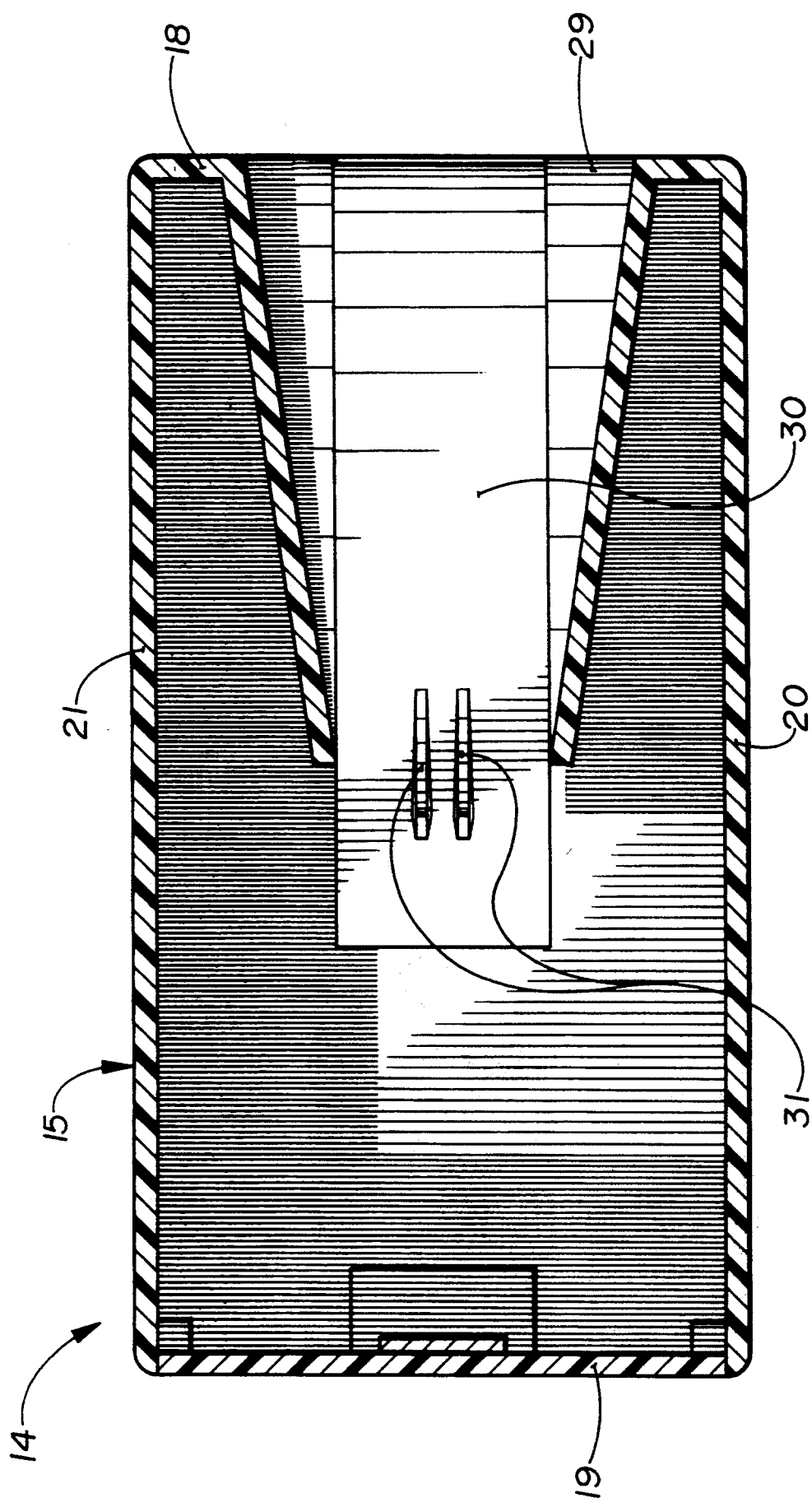
FIG. 7 is a cross-sectional view, taken along the lines 7—7 of FIG. 5 and drawn to an enlarged scale, and showing a pair of lanced out upwardly-projecting fingers on the leaf spring.
Figure 8:
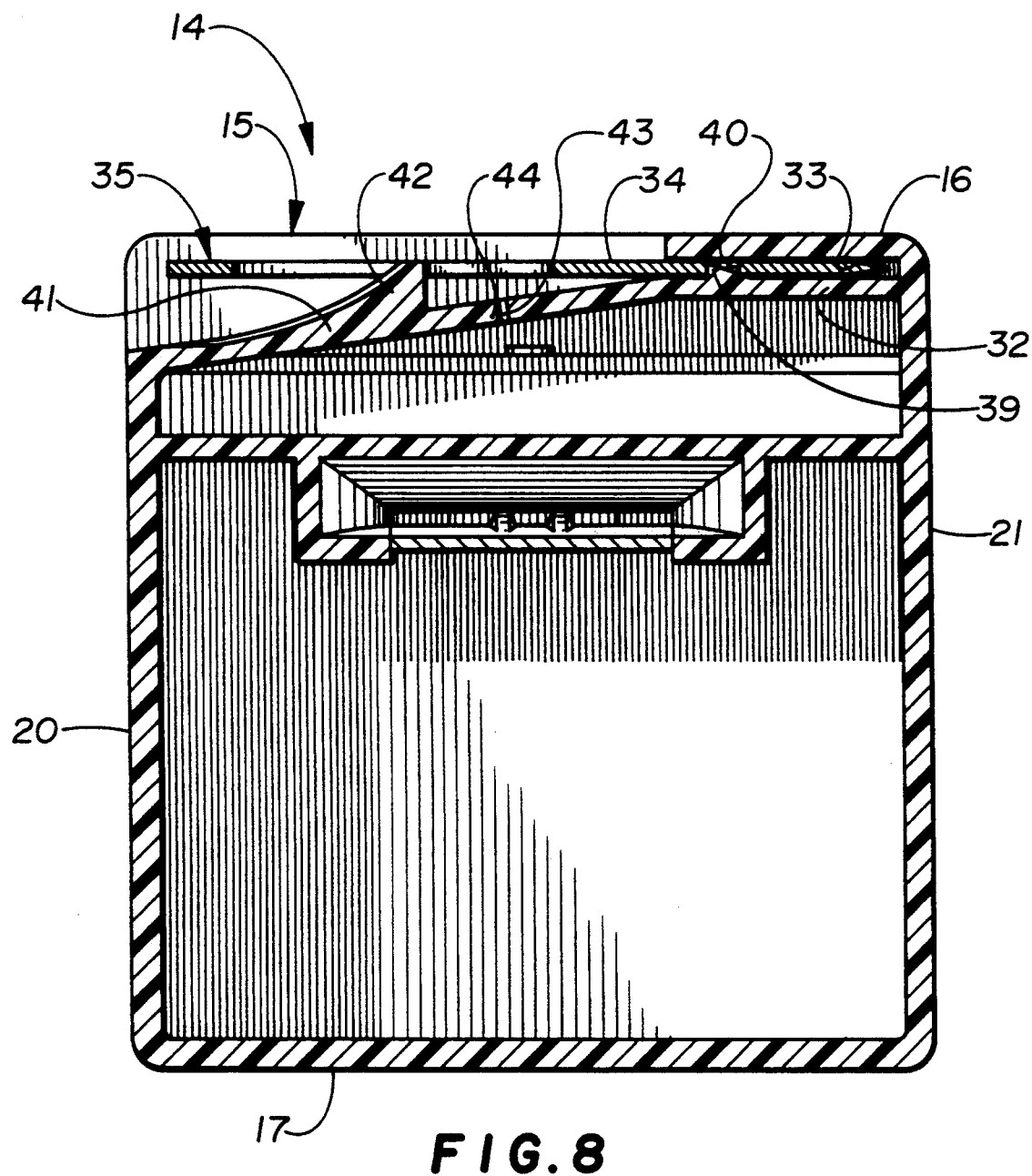
FIG. 8 is a cross-sectional view, taken along the lines 8—8 of FIG. 6, and showing the retention of a new blade in the housing.

With reference again to FIG. 5, and with further reference to FIG. 7, a leaf spring 30 is cantilever mounted on the bottom wall 17 of the housing by rivets 30A (or other suitable means) and the leaf spring 30 is disposed below the internal wall 23 in the housing 15, above the chamber 22 therein, and extends from the opening 29 in the front wall 18 of the housing 15 towards the rear wall 19 thereof. The leaf spring 30 has a pair of upwardly-projecting lanced-out fingers 31 formed thereon, as shown more clearly in FIGS. 5 and 7.

With reference again to FIGS. 6 and 8, the housing 15 of the blade dispenser 14 has a first interior wall 32 formed therein, recessed below the top wall 16 of the housing 15, and extending from the left side wall 21 of the housing 15 towards the right side wall 20 thereof. As a result, and as shown more clearly in FIG. 8, the top wall 16 of the housing 15 and the first interior wall 32 thereof define therebetween a slotted recess 33 in the housing 15 for receiving the forward portion 34 of a blade 35.

With reference to FIGS. 9–12, the blade 35 includes a rearward portion having a longitudinal slotted opening 36 formed therein. This opening 36 is conventional and includes a rearward portion 36A and a forward (narrower) portion 36B. The scalpel, on the other hand, has a forward portion provided with externally-accessible opposing slots or grooves 37A and 37B, respectively. In the usual practice of mounting the blade 35 on the forward portion of the scalpel 12, the blade 35 is flexed slightly so that the narrower forward portion 36B of the slotted opening 36 in the blade 35 is received in the grooves 37A and 37B of the scalpel 12.

Preferably, but not necessarily, the blade dispenser 14 of the present invention may find more particular utility in conjunction with a guarded scalpel $12^1$ (shown in FIG. 9). This guarded scalpel $12^1$, which is described and claimed in applicant's co-pending application Ser. No. 825,556 filed Jan. 24, 1992 for "SURGICAL SCALPEL WITH RETRACTABLE GUARD", has a sliding retractable guard 38 for alternatively covering and uncovering the blade 35. The sliding movement of the guard 38 is performed manually, using only one hand, and without requiring the surgeon (or other health care provider) to take his or her eyes off the patient.

With reference again to FIG. 8, the first interior wall 32 has a first upwardly-projecting hook 39 formed thereon; and the hook 39 is received in a circular hole 40 (or other suitable opening) formed in the blade 35, thereby positioning the blade 35 within the slotted recess 33 and preventing the blade 35 from engaging the left side wall 21 of the housing 15. This assures that the blade will remain sharp and will not be dulled, inadvertently, by engaging the walls of the housing 15 and, particularly, the left side wall 21. The housing 15 further has a second interior wall 41 formed therein, recessed below the top wall 16 of the housing 15, and extending from the right side wall 20 of the housing 15 towards the left side wall 21 thereof. The second interior wall 41 has a second upwardly-projecting hook 42 received within the slotted opening 36 in the rearward portion of the blade 35, further positioning and retaining the blade 35 in the housing 15. As shown more clearly in FIG. 8, the first interior wall 32 and the second interior wall 41 have inner extremities 43 and 44, respectively, which confront one another.

Figure 6:
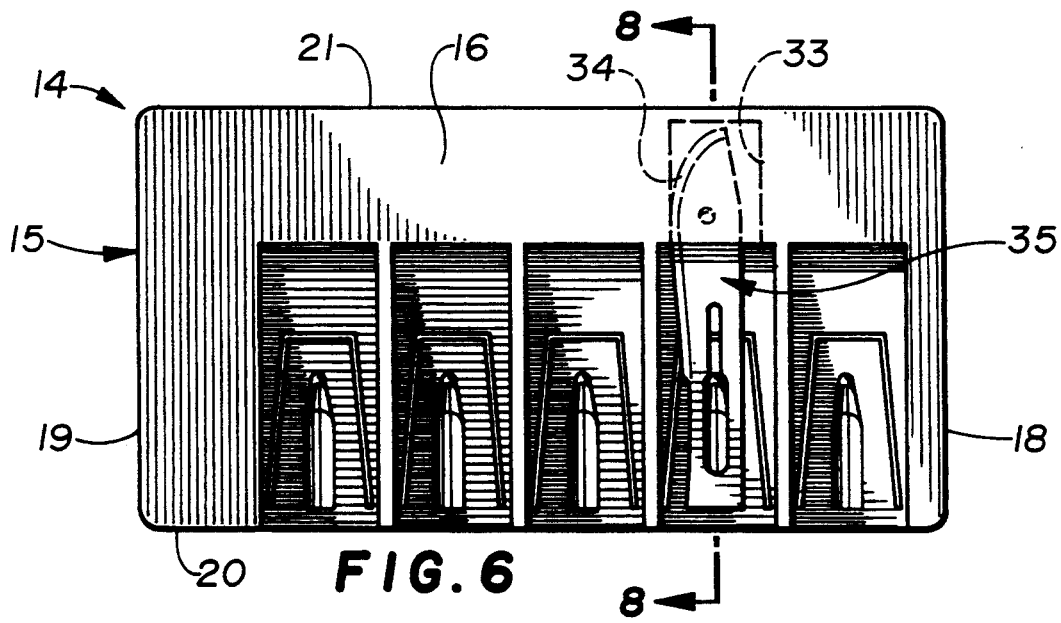
FIG. 6 is a top plan view of the housing of the blade dispenser of the present invention, showing one of the new or unused blades in the dispenser (it being understood that the blade dispenser is intended for a plurality of blades).

Preferably, and as shown more clearly in FIG. 6, the housing 15 of the blade dispenser 14 has five slotted recesses 33 for five blades 35, respectively, as well as five corresponding sets of first and second interior walls 32 and 41, respectively. However, it will be appreciated that any number of replacement blades 35 may be contained within the housing 15 of the blade dispenser 14, consonant with the teachings of the present invention.

Figure 13A:
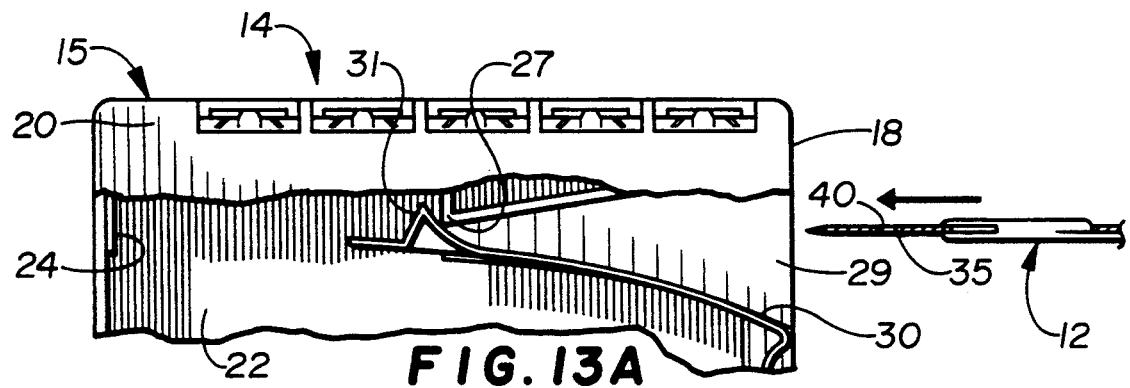
FIGS. 13A–13D are schematic sequence views, showing the manner in which the scalpel with an "old" or used blade may be quickly and conveniently inserted into the housing and withdrawn therefrom (in a sliding or reciprocating movement) to remove or "strip" the old used blade from the scalpel.
Figure 13B:
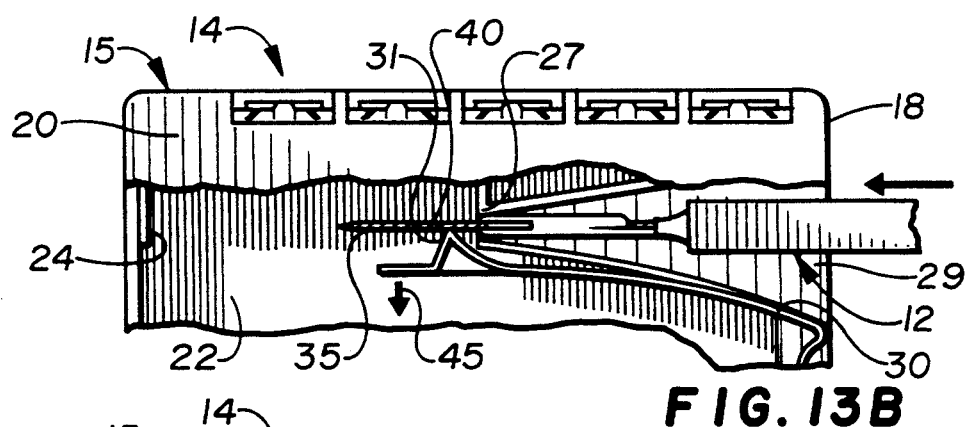
Figure 13C:
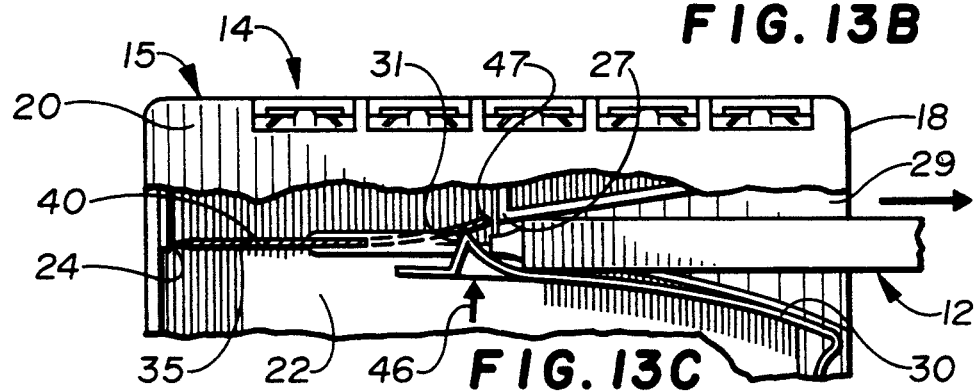
Figure 13D:
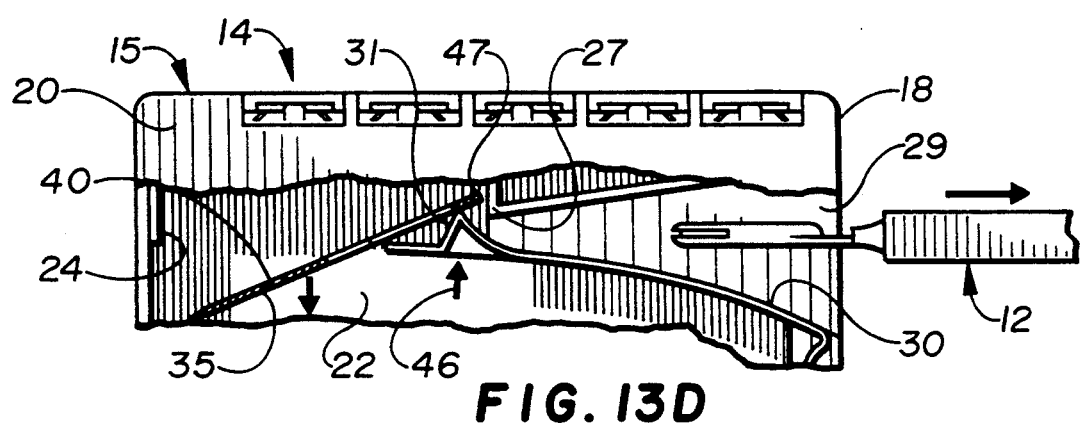

With reference to FIGS. 13A–13D, the sequence of removing or stripping an "old" or used blade 35 from the scalpel 12 will be readily understood. The scalpel 12 (with its used blade 35) is inserted through the opening 29 in the front wall 18 of the housing 15, as shown in FIG. 13A. Preferably, the opening 29 is tapered inwardly (as shown more clearly in FIG. 7) to facilitate insertion of the scalpel 12. As the scalpel 12 is inserted into the housing 15, the used blade 35 on the scalpel 12 deflects the leaf spring 30 downwardly in the housing 15, as shown by the downwardly-projecting arrow 45 in FIG. 13B, and clears the upwardly-projecting fingers 31 on the leaf spring 30 from the shoulder 27 on the interior wall 23 in the housing 15. Thereafter, as the scalpel 12 is withdrawn from the housing 15, as shown more clearly in FIG. 13C, the leaf spring 30 moves upwardly (as indicated by the upwardly-projecting arrow 46 in FIGS. 13C and 13D) such that the end edge 47 of the rearward portion of the blade 35 is bent upwardly (FIG. 13C) and becomes partially disengaged from the scalpel 12; and as the scalpel 12 is further withdrawn from the housing 15, the end edge 47 of the blade 35 encounters the shoulder 27 on the intermediate downwardly-projecting portion of the interior wall 23 in the housing 15, thereby stripping the blade 35 completely from the scalpel 12 as shown more clearly in FIG. 13D. Thereafter, the used blade 35 falls down into the chamber 22 in the housing 15 (and on to the bottom wall 17 thereof) for ultimate disposal with the housing 15 of the blade dispenser 14.

Figure 14A:
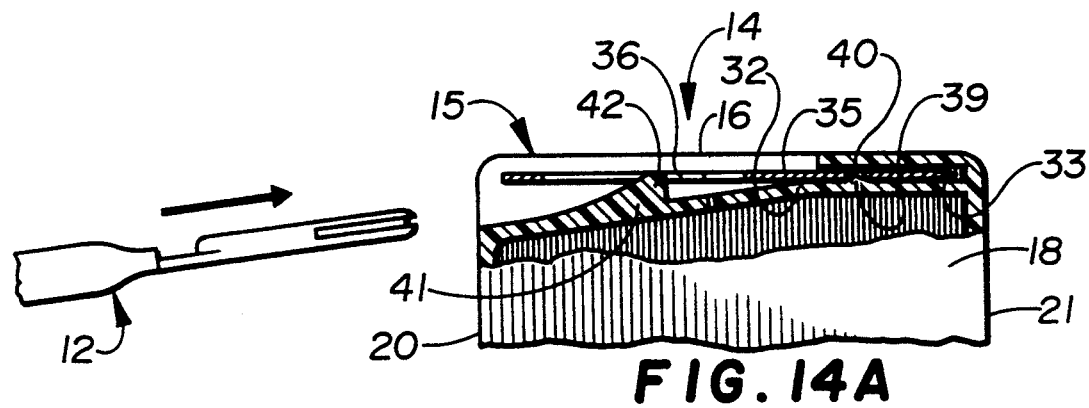
FIGS. 14A–14D are further schematic sequence views, showing the subsequent manner in which the "stripped" scalpel may be reinserted into the housing and withdrawn therefrom, again quickly and conveniently and in a sliding or reciprocating movement, to pick up a "new" or unused blade.
Figure 14B:
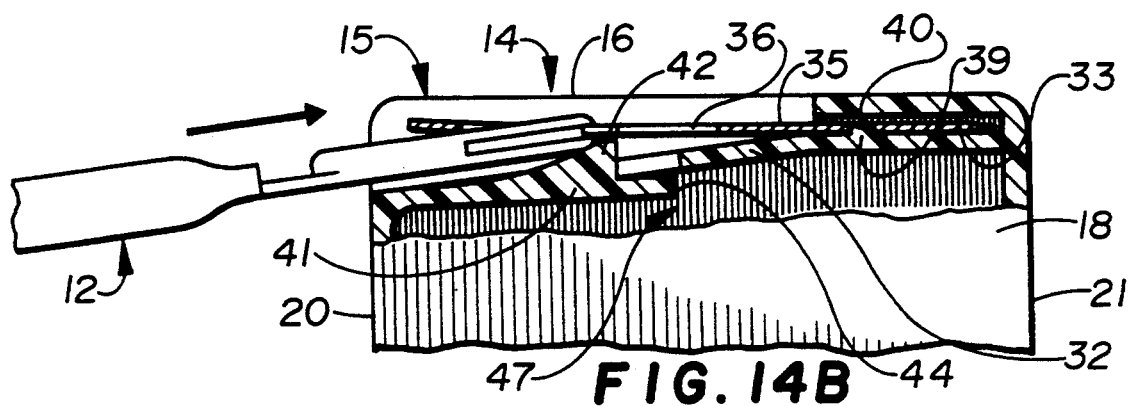
Figure 14C:
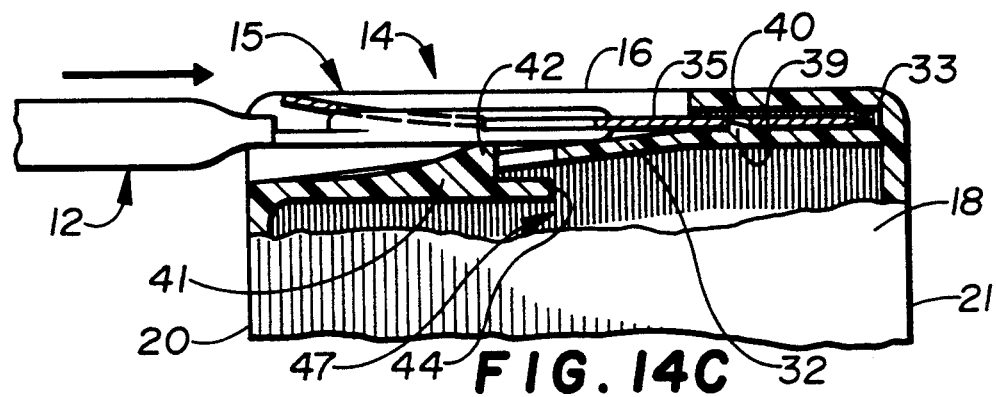
Figure 14D:
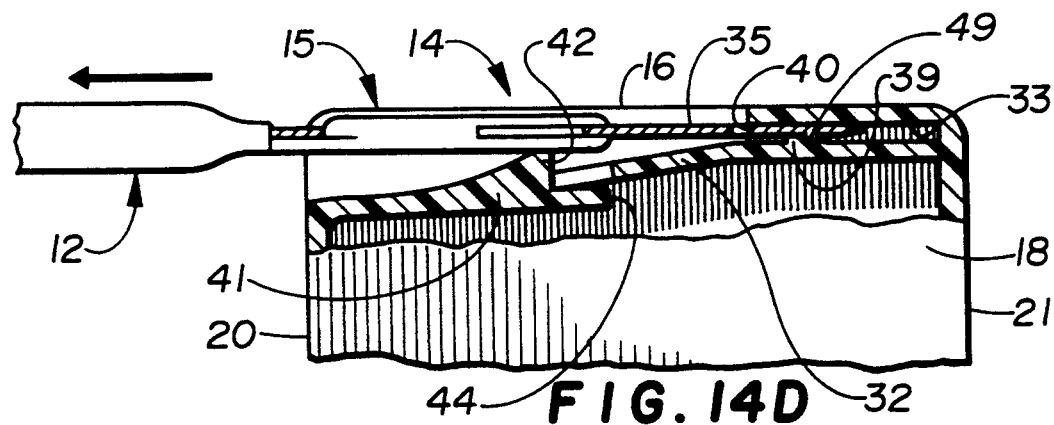

With reference to FIGS. 14A–14D, the sequence of mounting a new ("fresh" or unused) blade 35 on the scalpel 12 will be readily understood. The scalpel 12 (without any blade thereon) is inserted into the right side wall 20 of the housing 15 of the blade dispenser 14, as shown in FIG. 14A. Preferably, the opening in the wall 20 is tapered inwardly (as shown more clearly in FIGS. 6 and 8) to guide the scalpel 12 and facilitate its insertion into the blade dispenser 14. It will be understood by those skilled in the art that the scalpel 12 may be inserted into any suitable wall or opening in the housing 15, and that insertion into the right side wall 20 is only exemplary of the teachings of the present invention. With this in mind, as the scalpel 12 is inserted further into the housing 15, the forward portion of the scalpel 12 deflects the cantilevered second interior wall 41 downwardly, as indicated by the small downwardly-projecting arrow 47 in FIG. 14B, to disengage the second upwardly-projecting hook 42 from the longitudinal closed slotted opening 36 in the rearward portion of the blade 35. Simultaneously, the forward portion of the scalpel 12 is received in the slotted recess 33 in the housing 15; and as the scalpel 12 is inserted further into the housing 15, as shown in FIG. 14C, the forward portion of the scalpel 12 engages the rearward portion of the blade 35 (rearwardly of its slotted opening 36) and cams the rearward portion of the blade 35 upwardly (again as shown in FIG. 14C). Thereafter, and as shown in FIG. 14D, the forward portion of the scalpel 12 is received in the slotted opening 36 in the blade 35 to mount the blade 35 to the scalpel 12. As scalpel 12 is withdrawn from the housing 15 of the blade dispenser 14, the circular edge of the hole 40 in the forward portion 34 of the blade 35 engages the downwardly-sloping cam surface 49 on the hook 39 and downwardly deflects the cantilevered first interior wall 32 in the housing 15 (as shown more clearly in FIG. 14D) so that the hook 39 clears the hole 40 in the blade 35. Thereafter, the scalpel 12 (with the "new" blade 35 mounted thereon)

may be completely removed from the housing 15 of the blade dispenser 14.

Figure 17:
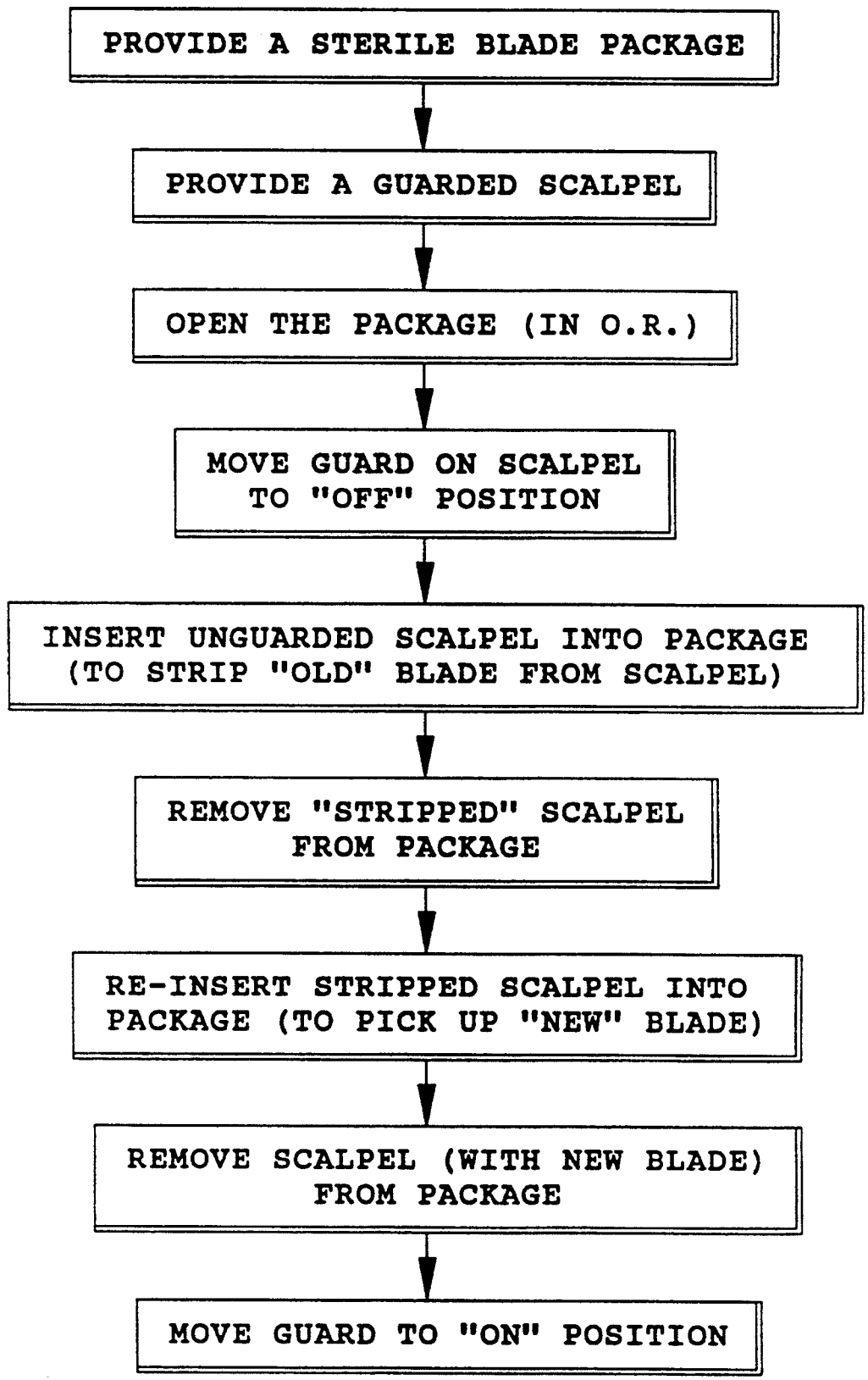
FIG. 17 is a flow chart illustrating the steps of the improved method of the present invention, as shown in the schematic sequence of FIGS. 15A–15J.

With reference to FIGS. 15A-15J and with further reference to FIGS. 16 and 17, the inherent features and advantages of the present invention will be more readily appreciated.

Figure 15D:
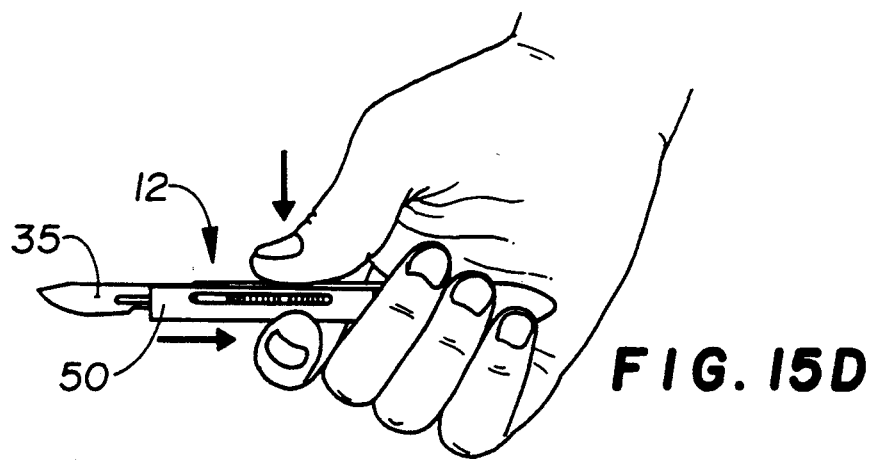

As shown in FIG. 15A, the present invention finds more particular utility with the guarded scalpel 12$^1$ having a guard 50. In FIGS. 15B and 15C, the sterile blade package 13 is removed to uncover the blade dispenser 14. The bottom wall 17 of the blade dispenser 14 may contain an adhesive 51 protected by a cover 52 (as shown in FIG. 16) and the cover 52 may be pulled away to enable the blade dispenser 14 to be removably mounted on the tray or cart 11 by means of the adhesive 51. In FIG. 15D, the guard 50 on the guarded scalpel 12$^1$ is manually retracted (in a one-hand operation) to expose the used or dulled blade 35.

Figure 15E:
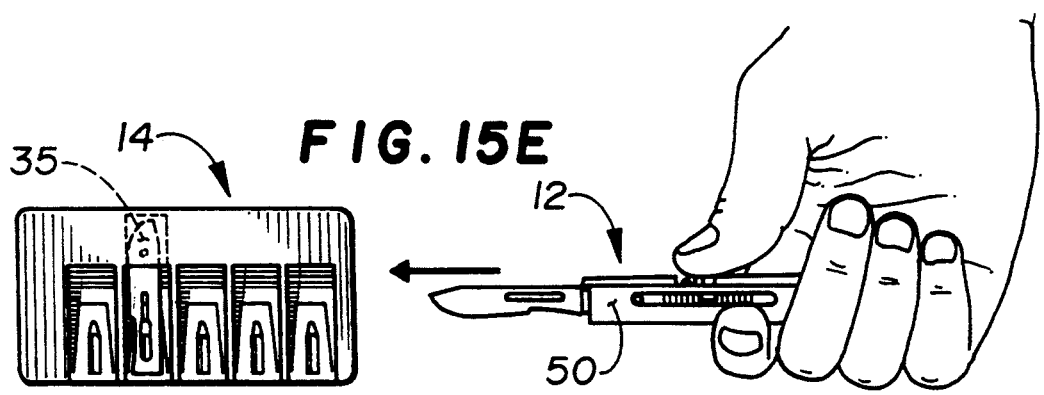
Figure 15F:
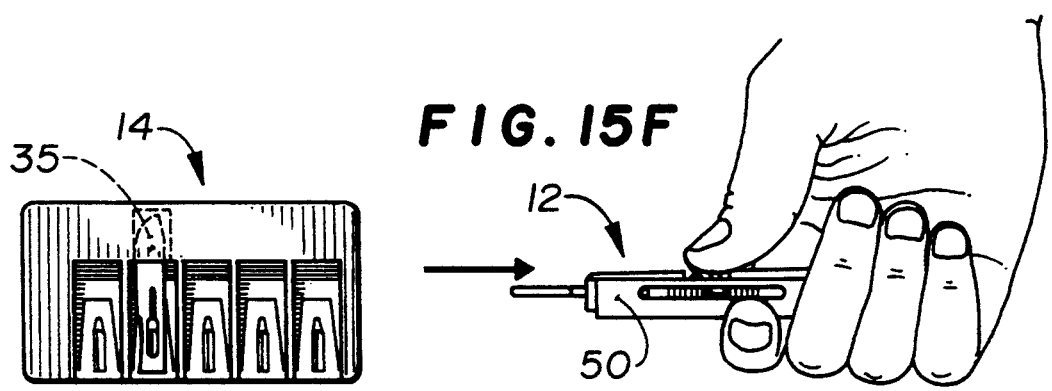
Figure 15G:
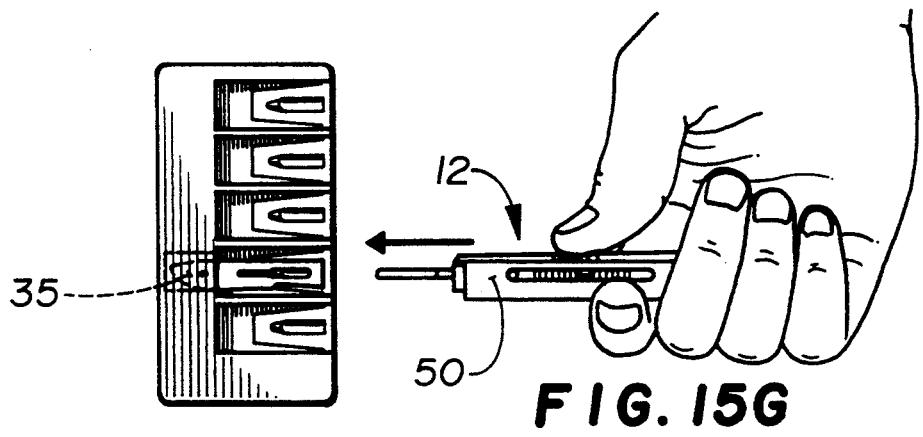
Figure 15H:
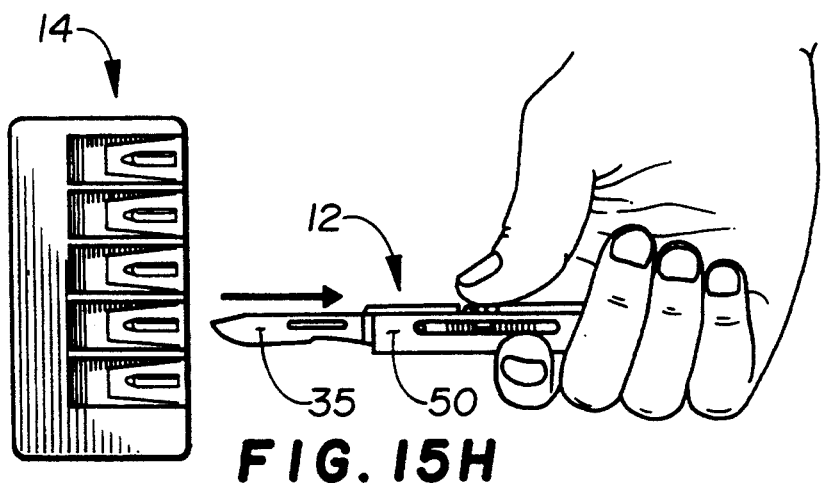
Figure 15I:
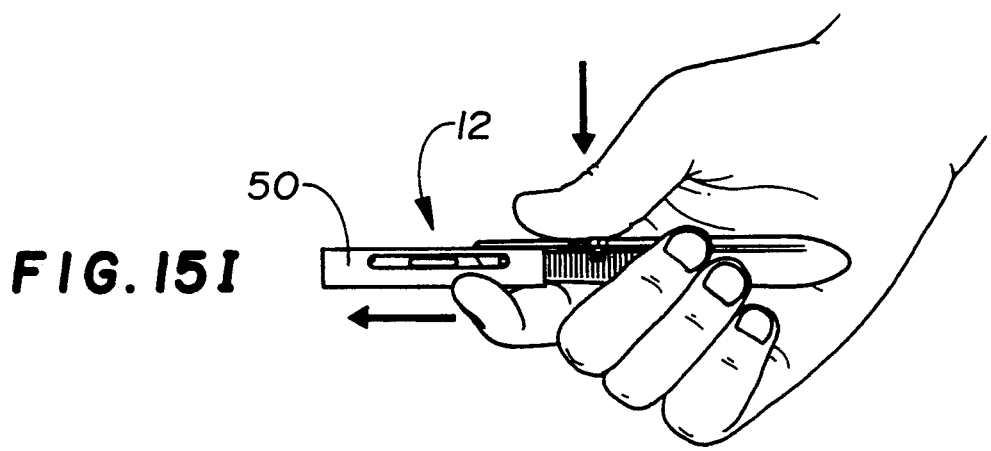

Thereafter, as shown in FIG. 15E, the scalpel 12$^1$ is inserted into the blade dispenser 14 and withdrawn therefrom (FIG. 15F) to remove the "old" or used blade 35 from the scalpel 12$^1$. The scalpel 12$^1$ is then re-inserted into the blade dispenser 14 (as shown in FIG. 15G) and withdrawn therefrom (FIG. 15H) to pick up a "new" or unused blade 35.

Figure 15J:
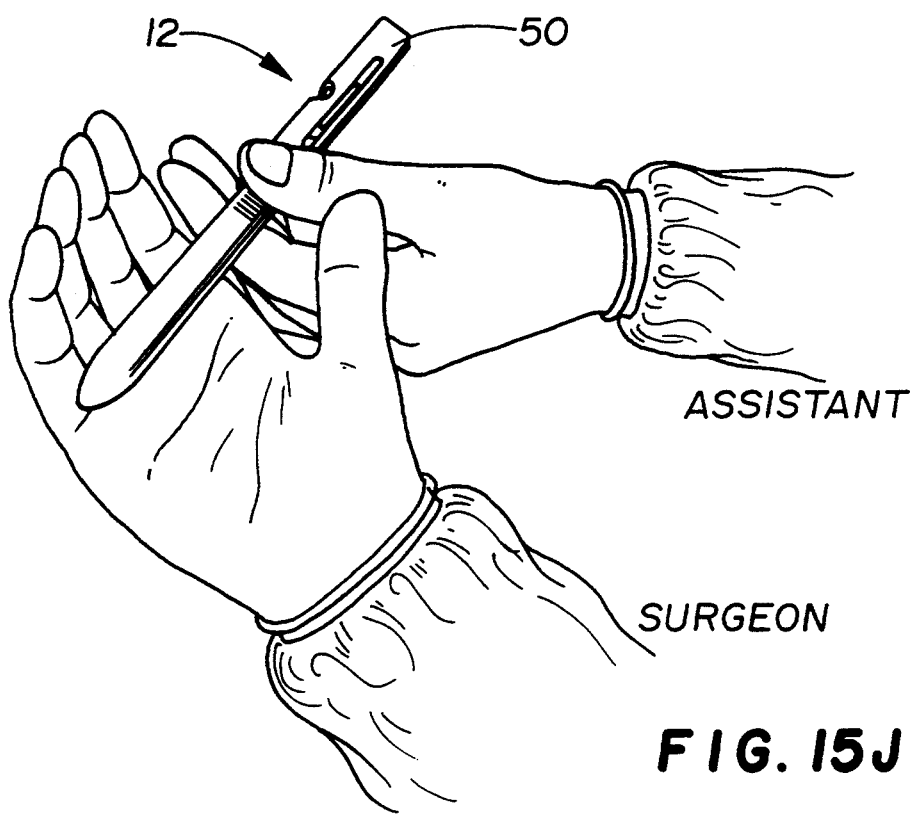

The guard 50 is moved forwardly to cover the blade 35 (FIG. 15I) and the guarded scalpel 12$^1$ is transferred from the assistant to the surgeon (FIG. 15J). This sequence is illustrated in the flow chart of FIG. 17.

As a result, the hazards of being cut or nicked while removing an old blade and mounting a new blade on the scalpel, or while transferring the scalpel during a surgical procedure, are substantially reduced (if not eliminated altogether). The risk —that health care providers will inadvertently acquire a virus or other blood-borne infectious disease during a surgical procedure—is considerably reduced. Additionally, this avoids periodic AIDS testing and counseling, which is both costly and inconvenient. Moreover, the anxiety levels of health care providers will be substantially reduced. Indeed, these present anxiety levels result in a kind of "Russian roulette" mentality, so that becoming infected becomes an accepted occupational hazard. That is distracting to the health care providers. The present invention alleviates those anxieties and distractions.

Obviously, many modifications may be made without departing from the basic spirit of the present invention.

For example, the sterile blade dispenser may be packaged as part of an overall kit. Moreover, the teachings of the present invention are not confined to the specific surgical blade disclosed herein, but are applicable to a wide variety of surgical blades; thus a plurality of blade dispensers may be used during a surgical procedure.

Also, in lieu of the adhesive to hold down the blade dispenser 14, it would be possible to hold the blade dispenser in one hand and to hold the scalpel in the other hand, while inserting the scalpel into the housing of the blade dispenser or else moving the housing over the scalpel.

Accordingly, it will be appreciated by those skilled in the art that within the scope of the appended claims, the invention may be practiced other than has been specifically described herein.

We claim:

1. A scalpel blade dispenser and disposal system for use during a surgical procedure in an operating room, comprising, in combination, a scalpel blade dispenser which includes a housing having at least one sterile blade therein, and wherein a scalpel has a blade which will be normally replaced during the surgical procedure to maintain good surgical cutting techniques, first means within the housing enabling the blade to be removed from the scalpel upon insertion and withdrawal of the scalpel from the housing, wherein the blade thereby removed from the scalpel is confined within the housing which is subsequently discarded, and second means within the housing enabling the sterile blade to be mounted upon the scalpel upon the subsequent re-insertion of the scalpel into the housing and withdrawal of the scalpel therefrom, wherein the second means comprises a first interior wall Cantilever mounted within the housing, a hook on the first interior wall, the sterile blade having a hole formed therein and receiving the hook on the first interior wall, thereby positioning the sterile blade on the wall, and cam means between the hook on the first interior wall and the hole in the sterile blade, such that as the scalpel with the sterile blade mounted thereon is withdrawn from the housing, the first interior wall deflects and is cammed away from the sterile blade, thereby clearing the hook from the hole in the sterile blade, and thereby allowing the scalpel with the sterile blade mounted thereon to be removed from the housing.

2. The combination of claim 1, further including a sterile package for the housing, the sterile package being removed prior to the surgical procedure.

3. The combination of claim 1, wherein a plurality of sterile blades are contained within the housing, wherein the housing has a plurality of discarded blades confined therein, and wherein the housing is disposed of following the surgical procedure.

4. The combination of claim 1, wherein the blade on the scalpel has a back edge, and wherein the first means comprises a leaf spring in the housing, the spring having an upwardly-projecting finger formed thereon, a second wall in the housing, and the second wall having a downwardly-projecting shoulder formed thereon and engaging the finger on the leaf spring; such that as the scalpel with the blade mounted thereon is inserted into the housing, the blade deflects the leaf spring, thereby clearing the finger from the shoulder as the blade is moved past the shoulder on the second wall; and such that as the scalpel is withdrawn from the housing, the back edge of the blade engages the shoulder on the second wall to strip the blade from the scalpel.

5. The combination of claim 1, wherein the housing is substantially rectangular and includes top and bottom walls, front and rear walls, and right side and left side walls, respectively, wherein the blade is removed upon insertion of the scalpel into the front wall of the housing and withdrawal of the scalpel therefrom, and wherein the sterile blade is mounted upon the scalpel upon the subsequent re-insertion of the scalpel into the right side wall of the housing and withdrawal of the scalpel therefrom.

6. The combination of claim 1, further including a guard slidably mounted on the scalpel, the guard being alternatively retracted and advanced to uncover and cover the blade, respectively, and in a one-handed operation.

7. A scalpel blade dispenser and disposal system for use during a surgical procedure in an operating room, wherein a scalpel is used during the surgical procedure, the scalpel having a blade mounted thereon, the system comprising a surgical blade dispenser including a housing having at least one blade therein, and wherein the blades on a scalpel are normally replaced during the procedure to maintain good surgical cutting techniques, the improvement comprising a sterile package for the housing, the sterile package being removed prior to the surgical procedure, the housing being substantially rectangular and including top and bottom walls, front and rear walls, and right side and left side walls, respectively, first means within the housing enabling the blade to be removed from the scalpel upon insertion of the scalpel into the front wall of the housing and withdrawal therefrom, wherein the blade thereby removed from the scalpel is confined within the housing which is subsequently discarded, said first means comprising a leaf spring in the housing and having an upwardly-projecting finger formed thereon, and a wall in the housing, the wall having a downwardly-projecting shoulder formed thereon and engaging the finger on the leaf spring; such that as the scalpel with the blade mounted thereon is inserted into the housing, the blade deflects the leaf spring, clearing the finger from the shoulder as the blade is moved past the shoulder on the wall; and such that as the scalpel is withdrawn from the housing, the back edge of the blade engages the shoulder on the wall to strip the blade from the scalpel, a plurality of sterile blades in the housing, and second means within the housing enabling at least one sterile blade to be mounted upon the scalpel upon subsequent re-insertion of the scalpel into the right side wall of the housing and withdrawal of the scalpel therefrom, said second means comprising a first interior wall cantilever mounted within the housing, a hook on the wall, the sterile blade having a hole formed therein and receiving the hook on the wall, thereby positioning the sterile blade on the wall, and cam means between the hook on the first interior wall and the hole in the sterile blade, such that as the scalpel with the sterile blade mounted thereon is withdrawn from the housing, the first interior wall deflects and is cammed away from the blade, thereby clearing the hook from the hole in the blade, and thereby allowing the scalpel with the sterile blade mounted thereon to be removed from the housing.

8. A scalpel blade dispenser and disposal system for use during a surgical procedure in an operating room, wherein a scalpel provided with a blade is used, and wherein the dispenser is provided with a plurality of sterile blades for the scalpel, the blade on the scalpel being normally replaced during the procedure to maintain good surgical cutting techniques, comprising, in combination, a housing, a sterile package for the housing, the sterile package being removed prior to the surgical procedure, the housing being substantially rectangular and including top and bottom walls, front and rear walls, and right side and left side walls, respectively, first means within the housing enabling the blade to be removed from the scalpel upon insertion of the scalpel into the front wall of the housing and withdrawal therefrom, wherein the blade thereby removed from the scalpel is confined within the housing which is subsequently discarded and second means within the housing enabling a selected sterile blade to be mounted upon the scalpel upon subsequent re-insertion of the scalpel into the right side wall of the housing and withdrawal of the scalpel therefrom, wherein the blade has a rear edge portion, and wherein the front wall portion of the housing has an opening formed therein for slidable insertion of the scalpel with the blade to be removed therefrom, further including a second internal wall within the housing, the second internal wall having a portion sloping downwardly from the top wall towards the bottom wall of the housing and from the opening in the front wall to the rear wall thereof, thereby defining a shoulder on the second internal wall, a leaf spring mounted within the housing and projecting upwardly from the bottom wall towards the top wall, below the second internal wall in the housing, and from the opening in the front wall towards the rear wall of the housing, the leaf spring contacting the shoulder on the second internal wall in the housing, and the leaf spring having at least one upwardly-projecting finger rearwardly of the shoulder on the second internal wall; such that upon insertion of a scalpel with the blade thereon through the opening in the front wall of the housing, the scalpel depresses the leaf spring, and the upwardly-projecting finger on the leaf spring lifts the blade up and away from the scalpel; and such that upon withdrawal of the scalpel from the housing, the shoulder on the second internal wall in the housing engages the rear edge portion of the blade and strips the blade off the scalpel, such that the blade falls down into the housing and on to the bottom wall thereof.

9. The combination of claim 8, wherein two upwardly-projecting fingers are formed on the leaf spring, the fingers being parallel to, and spaced apart from, each other.

10. A scalpel blade dispenser and disposal system for use during a surgical procedure in an operating room, wherein a scalpel provided with a blade is used, and wherein the dispenser is provided with a plurality of sterile blades for the scalpel, the blade on the scalpel being normally replaced during the procedure to maintain good surgical cutting techniques, comprising, in combination, a housing, a sterile package for the housing, the sterile package being removed prior to the surgical procedure, the housing being substantially rectangular and including top and bottom walls, front and rear walls, and right side and left side walls, respectively, first means within the housing enabling the blade to be removed from the scalpel upon insertion of the scalpel into the front wall of the housing and withdrawal therefrom, wherein the blade thereby removed from the scalpel is confined within the housing which is subsequently discarded and second means within the housing enabling a selected sterile blade to be mounted upon the scalpel upon subsequent re-insertion of the scalpel into the right side wall of the housing and withdrawal of the scalpel therefrom, wherein the scalpel has a forwardly-projecting portion, and wherein the selected sterile blade has a slotted opening formed therein to receive the forwardly-projecting portion of the scalpel, thereby removably mounting the sterile blade to the scalpel, the sterile blade further having a forward portion provided with a hole forwardly of the slotted opening formed in the sterile blade, the housing having at least one first interior wall formed therein, recessed below the top wall of the housing, and extending from the left side wall of the housing towards the right side wall thereof, the top wall and the first interior wall thereby defining therebetween a slotted recess in the housing, such that the forward portion of the sterile blade may be received within the slotted recess in the housing, the first interior wall having a first upwardly-projecting hook received within the hole formed in the forward portion of the sterile blade, thereby positioning the sterile blade within the slotted recess in the housing and preventing the sterile blade from being dulled by engaging the left side wall of the housing, the hole in the sterile blade having a circular edge, the housing further having at least one second interior wall, extending towards the first interior wall, and from the right side wall of the housing towards the left side wall thereof, and the second interior wall having a second upwardly-projecting hook engaging the slotted opening in the sterile blade, such that upon re-insertion of the scalpel within the housing, the forward portion of the scalpel downwardly deflects the second interior wall and disengages the second upwardly-projecting hook on the second interior wall from the slotted opening in the sterile blade, such that the laterally-projecting portion of the scalpel engages and is received within the slotted opening in the sterile blade, thereby mounting the sterile blade to the scalpel, and the first upwardly-projecting hook on the first interior wall having an upward surface sloping downwardly towards the left side wall of the housing, such that as the scalpel with the sterile blade thereon is withdrawn out of the housing in a sliding movement from the left side wall to the right side wall of the housing, the circular edge on the hole in the forward portion of the sterile blade engages the upward sloping surface on the first upwardly-projecting hook on the first interior wall, thereby deflecting and camming the first interior wall downwardly within the housing to release the first upwardly-projecting hook from the hole in the forward portion of the sterile blade, and thereby enabling the scalpel and sterile blade to be completely withdrawn from the housing.

11. In a dispenser for the blade of a surgical scalpel, wherein the scalpel has a forwardly-projecting portion provided with a laterally-projecting longitudinal rib, and wherein the blade has a slot formed therein to receive the laterally-projecting longitudinal rib on the forwardly-projecting portion of the scalpel, thereby removably mounting the blade to the scalpel, the blade having a cutting edge formed thereon, and wherein the dispenser includes a housing provided with an opening through which the forwardly-projecting portion of the scalpel is inserted, the improvement which comprises a cantilevered first wall within the housing, extending towards the opening therein, and defining a slotted recess in the housing, a sterile blade within the slotted recess, the sterile blade having a hole formed therein, a first hook on the first wall and received in the hole in the sterile blade, a cantilevered second wall in the housing, below the opening, and extending towards the first wall, the second wall having a second hook received in the slot in the sterile blade, thereby retaining the sterile blade within the slotted recess in the housing and thereby preventing the cutting edge on the sterile blade from becoming dulled inadvertently, such that upon insertion of the forwardly-projecting portion of the scalpel within the opening in the housing, the forwardly-projecting portion of the scalpel downwardly deflects the second wall and disengages the second hook from the slot in the sterile blade, such that the laterally-projecting longitudinal rib on the scalpel engages and is received within the slot in the sterile blade, thereby mounting the sterile blade to the scalpel, and the first hook on the first wall having a sloping surface, such that as the scalpel with the sterile blade thereon is withdrawn out of the opening in the housing, the hole in the sterile blade engages the sloping surface on the first hook on the first wall, thereby camming the first wall within the housing to release the first hook from the hole in the sterile blade, and thereby enabling the scalpel and sterile blade to be completely withdrawn from the housing.

12. In combination, a scalpel handle having a first blade mounted thereon, a housing having a sterile second blade therein, the sterile second blade having a cutting edge, positioning means between the housing and the sterile second blade so that the cutting edge on the sterile second blade is spaced from the housing, thereby precluding the cutting edge on the sterile second blade from being dulled inadvertently, first means including a first deflectable member in the housing and engaging the first blade on the scalpel handle for stripping the first blade from the scalpel handle upon insertion of the scalpel handle into the housing and withdrawal therefrom, and second means including a second deflectable member in the housing and engaging the sterile second blade to mount the sterile second blade on the scalpel handle as the scalpel handle is re-inserted into the housing, enabling the scalpel handle with the sterile second blade mounted thereon to be withdrawn from the housing.

* * * * *